United States Patent
Ghalili et al.

(10) Patent No.: US 11,622,944 B2
(45) Date of Patent: *Apr. 11, 2023

(54) STABILIZED MENTHOL AND OTHER VOLATILE COMPOUND COMPOSITIONS AND METHODS

(71) Applicants: Babak Ghalili, New York, NY (US); Arthur Goldberg, Livingston, NJ (US); John Borja, Keyport, NJ (US)

(72) Inventors: Babak Ghalili, New York, NY (US); Arthur Goldberg, Livingston, NJ (US); John Borja, Keyport, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/160,998

(22) Filed: Jan. 28, 2021

(65) Prior Publication Data

US 2021/0236436 A1  Aug. 5, 2021

Related U.S. Application Data

(60) Provisional application No. 62/981,772, filed on Feb. 26, 2020, provisional application No. 62/968,249, filed on Jan. 31, 2020.

(51) Int. Cl.
| | | |
|---|---|---|
| A61K 31/045 | (2006.01) | |
| A61K 47/12 | (2006.01) | |
| A61K 47/44 | (2017.01) | |
| A23L 33/105 | (2016.01) | |
| A23G 3/48 | (2006.01) | |
| A23G 3/40 | (2006.01) | |
| A23L 27/20 | (2016.01) | |
| A23L 33/12 | (2016.01) | |

(52) U.S. Cl.
CPC ............ *A61K 31/045* (2013.01); *A23G 3/40* (2013.01); *A23G 3/48* (2013.01); *A23L 27/203* (2016.08); *A23L 27/2028* (2016.08); *A23L 33/105* (2016.08); *A23L 33/12* (2016.08); *A61K 47/12* (2013.01); *A61K 47/44* (2013.01); *A23V 2002/00* (2013.01)

(58) Field of Classification Search
CPC ...... A61K 31/045; A61K 47/12; A61K 47/44; A23L 33/12; A23L 33/105; A23L 27/2028; A23L 27/203; A23G 3/48; A23G 3/40; A23V 2002/00
See application file for complete search history.

(56) References Cited

U.S. PATENT DOCUMENTS

| | | | |
|---|---|---|---|
| 4,117,110 A | | 9/1978 | Hautmann |
| 5,869,087 A | * | 2/1999 | Hirano ............... A61K 31/405 |
| | | | 424/449 |
| 6,495,097 B1 | | 12/2002 | Streit et al. |
| 7,993,635 B2 | | 8/2011 | Hamawaki et al. |
| 8,741,275 B2 | | 6/2014 | Dente et al. |
| 9,839,693 B2 | | 12/2017 | Borja et al. |
| 9,999,602 B2 | | 6/2018 | Vieth et al. |
| 2019/0110981 A1 | | 4/2019 | Weimann |
| 2020/0316151 A1 | | 10/2020 | Ghalili et al. |

OTHER PUBLICATIONS

PCT, Notification of Transmittal of the International Search Report and the Written Opinion of the International Searching Authority, or the Declaration, Application No. PCT/US21/15467, dated May 4, 2021, 15 pages.
Krizek et al, "Menthol-based hydrophobic deep eutectic solvents: Towards greener and efficient extraction of phytocannabinoids", Journal of Cleaner Production, 193 (2018) 391-396, 6 pages.
Al-Akayleh, "Therapeutic deep eutectic system of capric acid and menthol: Characterization and pharmaceutical application", Journal of Drug Delivery Science and Technology 53 (2019) 1-10, 10 pages.
Muzenda "Interactions of Polar and Nonpolar volatile organic compounds with methyl Ester solvents" 3rd International Conference on Medical Sciences and Chemical Engineering (ICMSCE'2013) Dec. 25-26, 2013 Bangkok (Thailand), 22-26, 5 pages.
International Search Report and Written Opinion of the International Searching Authority, United States Patent and Trademark Office, Application No. PCT/US2021/015467, dated Jan. 28, 2021, 15 pages.

* cited by examiner

*Primary Examiner* — Snigdha Maewall
(74) *Attorney, Agent, or Firm* — Ziegler IP Law Group LLC

(57) ABSTRACT

The present disclosure relates to a stabilized or more stable volatile compound, e.g., menthol, compositions and methods of making and using them including a mixture of a stabilizer compound of formula (I), for example, undecylenic acid methyl ester, undecylenic acid or a salt thereof and a volatile compound where the volatile compound is less susceptible to volatizing into a gas.

Formula (I)

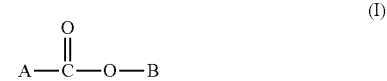

(I)

wherein A is —$(CH_2)_a$-CH=CH—$(CH_2)_{5-a}$-H where a is from 0 to 5,
—$(CH_2)_b$-CH=CH—$(CH_2)_{6-b}$-H where b is from 0 to 6,
—$(CH_2)_c$-CH=CH—$(CH_2)_{7-c}$-H where c is from 0 to 7,
—$(CH_2)_d$-CH=CH—$(CH_2)_{8-d}$-H where d is from 0 to 8, or
—$CH_2)_e$-CH=CH—$(CH_2)_{9-d}$-H where d is from 0 to 9;
B is hydrogen or $C_{1-5}$ alkyl; and pharmaceutically acceptable salts thereof where B is hydrogen.

20 Claims, No Drawings

STABILIZED MENTHOL AND OTHER VOLATILE COMPOUND COMPOSITIONS AND METHODS

CROSS-REFERENCE TO RELATED APPLICATIONS

This application claims priority to and the benefit of U.S. Provisional Patent Application Ser. No. 62/968,249 filed Jan. 31, 2020 and U.S. Provisional Patent Application Ser. No. 62/981,772 filed Feb. 26, 2020, the disclosures of which are incorporated herein by reference in their entirety.

FIELD

The aspects of the present disclosure relate to compositions and methods including stabilized or more stable volatile compounds, e.g., menthol.

BACKGROUND

Menthol is a terpene that is known to have a high vapor pressure at normal temperature. As a result of the high vapor pressure, menthol, as well as other highly volatile aromatic compounds, e.g., volatile compounds, can be difficult to work with and formulate with because its high vapor pressure causes them to be very volatile and convert easily to a gas from either a solid state or dissolved in a liquid solution. As a result, compositions including menthol and other highly volatile aromatic compounds are not stable in the amount in which they are included therein and over time the amount of menthol and other highly volatile aromatic compounds present when the compositions are formed or the amount of menthol originally added in making such a composition will volatilize to a gas and escape.

Various emulsion and encapsulation methods have been used to prevent the menthol in menthol containing compositions to volatize and escape from such menthol containing composition. For example, different encapsulation compositions and methods have been used to prevent such volatilization including, for example, various cyclodextrins that include a hydrophobic inside and a hydrophilic outside.

SUMMARY

In one embodiment, a stabilized or more stable menthol composition is provided. The stabilized or more stable menthol composition comprises, consists or consists essentially of menthol; and at least one menthol stabilizer compound, the at least one menthol stabilizer compound including undecylenic acid (10-undecenoic acid), a salt of undecylenic acid and undecylenic acid methyl ester (methyl 10-undecenoate); and optionally a solvent.

In another embodiment, a stabilized or more stable menthol composition is provided. The stabilized or more stable menthol composition comprises, consists or consisting essentially of menthol; and at least one menthol stabilizer compound, the at least one menthol stabilizer compound including undecylenic acid (10-undecenoic acid) a salt of undecylenic acid or undecylenic acid methyl ester (methyl 10-undecenoate); and optionally a solvent capable of dissolving the menthol.

In another embodiment, a composition is provided. The composition includes a stabilized or more stable menthol composition that comprises, consists or consists essentially of menthol; at least one menthol stabilizer compound, the at least one menthol stabilizer compound including undecylenic acid (10-undecenoic acid), a salt of undecylenic acid and undecylenic acid methyl ester (methyl 10-undecenoate); and optionally a solvent capable of dissolving the menthol; and at least one of a pharmaceutically active agent and a delivery vehicle, wherein the stabilized or more stable menthol composition is formed prior to being added to the at least one of the pharmaceutically active agent and the delivery vehicle.

In another embodiment, a method of forming a stabilized or more stable menthol composition is provided. The method comprises, consists or consists essentially of mixing menthol; and at least one menthol stabilizer compound, the at least one menthol stabilizer compound including undecylenic acid (10-undecenoic acid), a salt of undecylenic acid, and undecylenic acid methyl ester (methyl 10-undecenoate).

In another embodiment, a stabilized or more stable volatile compound composition is provided. The stabilized or more stable volatile compound composition comprises, consists or consisting essentially of one or more volatile compounds; and at least one stabilizer compound of the formula

wherein A is —(CH2)$_a$-CH=CH—(CH 2)$_{5-a}$-H where a is from 0 to 5,
—(CH2)$_b$-CH=CH—(CH 2)$_{6-b}$-H where b is from 0 to 6,
—(CH2)$_c$-CH=CH—(CH 2)$_{7-c}$-H where c is from 0 to 7,
—(CH2)$_d$-CH=CH—(CH 2)$_{8-d}$-H where d is from 0 to 8, or
—CH2)$_e$-CH=CH—(CH 2)$_{9-d}$-H where d is from 0 to 9;
B is hydrogen or C$_{1-5}$ alkyl; and pharmaceutically acceptable salts thereof where B is hydrogen; and optionally a solvent.

In another embodiment, a stabilized or more stable volatile compound composition is provided. The stabilized or more stable volatile compound composition comprises, consists or consisting essentially of one or more volatile compounds; and at least one stabilizer compound of the formula

wherein A is —(CH2)$_a$-CH=CH—(CH 2)$_{5-a}$-H where a is from 0 to 5,
—(CH2)$_b$-CH=CH—(CH 2)$_{6-b}$-H where b is from 0 to 6,
—(CH2)$_c$-CH=CH—(CH 2)$_{7-c}$-H where c is from 0 to 7,
—(CH2)$_d$-CH=CH—(CH 2)$_{8-d}$-H where d is from 0 to 8, or
—CH2)$_e$-CH=CH—(CH 2)$_{9-d}$-H where d is from 0 to 9;
B is hydrogen or C$_{1-5}$ alkyl; and pharmaceutically acceptable salts thereof where B is hydrogen; and optionally a solvent capable of dissolving the one or more volatile compounds.

In another embodiment, a composition is provided. The composition includes a stabilized or more stable volatile compound composition that comprises, consists or consists essentially of a stabilized or more stable volatile compound composition; and at least one stabilizer compound of the formula

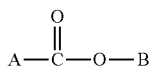

(I)

wherein A is —(CH2)$_a$-CH=CH—(CH 2)$_{5-a}$-H where a is from 0 to 5,
—(CH2)$_b$-CH=CH—(CH 2)$_{6-b}$-H where b is from 0 to 6,
—(CH2)$_c$-CH=CH—(CH 2)$_{7-c}$-H where c is from 0 to 7,
—(CH2)$_d$-CH=CH—(CH 2)$_{8-d}$-H where d is from 0 to 8, or
—CH2)$_e$-CH=CH—(CH 2)$_{9-d}$-H where d is from 0 to 9;
B is hydrogen or C$_{1-5}$ alkyl; and pharmaceutically acceptable salts thereof where B is hydrogen; and optionally a solvent capable of dissolving the one or more volatile compounds;
and at least one of a pharmaceutically active agent and a delivery vehicle, wherein the stabilized or more stable volatile compound composition is formed prior to being added to the at least one of the pharmaceutically active agent and the delivery vehicle.

In another embodiment, a composition is provided. The composition includes a stabilized or more stable volatile compound composition that comprises, consists or consists essentially of a stabilized or more stable volatile compound composition including a pre-formed mixture of one or more volatile compounds and at least one stabilizer compound of the formula

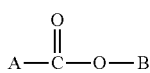

(I)

wherein A is —(CH2)$_a$-CH=CH—(CH 2)$_{5-a}$-H where a is from 0 to 5,
—(CH2)$_b$-CH=CH—(CH 2)$_{6-b}$-H where b is from 0 to 6,
—(CH2)$_c$-CH=CH—(CH 2)$_{7-c}$-H where c is from 0 to 7,
—(CH2)$_d$-CH=CH—(CH 2)$_{8-d}$-H where d is from 0 to 8, or
—CH2)$_e$-CH=CH—(CH 2)$_{9-d}$-H where d is from 0 to 9;
B is hydrogen or C$_{1-5}$ alkyl; and pharmaceutically acceptable salts thereof where B is hydrogen; and at least one of a pharmaceutically active agent and a delivery vehicle, wherein the stabilized or more stable volatile compound composition is formed prior to being added to the at least one of the pharmaceutically active agent and the delivery vehicle.

In another embodiment, a method of forming a stabilized or more stable volatile compound composition is provided. The method comprises, consists or consists essentially of mixing one or more volatile compounds and at least one stabilizer compound of the formula

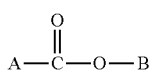

(I)

wherein A is —(CH2)$_a$-CH=CH—(CH 2)$_{5-a}$-H where a is from 0 to 5,
—(CH2)$_b$-CH=CH—(CH 2)$_{6-b}$-H where b is from 0 to 6,
—(CH2)$_c$-CH=CH—(CH 2)$_{7-c}$-H where c is from 0 to 7,
—(CH2)$_d$-CH=CH—(CH 2)$_{8-d}$-H where d is from 0 to 8, or
—CH2)$_e$-CH=CH—(CH 2)$_{9-d}$-H where d is from 0 to 9;
B is hydrogen or C$_{1-5}$ alkyl; and pharmaceutically acceptable salts thereof where B is hydrogen.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by embodiments of the present disclosure. As used herein, "about" may be understood by persons of ordinary skill in the art and can vary to some extent depending upon the context in which it is used. If there are uses of the term which are not clear to persons of ordinary skill in the art, given the context in which it is used, "about" may mean up to plus or minus 10% of the particular term.

The terms "%", "% by weight", "weight %" and "wt %" are all intended to mean unless otherwise stated, percents by weight based upon a total weight of 100% end composition weight. Thus 10% by weight means that the component constitutes 10 wt. parts out of every 100 wt. parts of total composition.

The term "pharmaceutically acceptable" means that which is useful in preparing a pharmaceutical composition that is generally non-toxic and is not biologically undesirable and includes that which is acceptable for veterinary use and/or human pharmaceutical use.

The term "orally acceptable" means the compound, substance, composition, formulation or device may be administered to or into the oral cavity and/or surfaces of the oral cavity of an animal (e.g., a human), including the teeth and gums, without substantial harmful effects to the oral cavity and/or its surfaces as well as can be ingested into the gastrointestinal tract without substantial harmful effects thereto.

The term "topically acceptable" or "topical delivery" means the compound, substance or device may be administered to or onto the surface of an animal (e.g., a human), including the skin or other accessible tissues, without substantial harmful effects to the body part and/or its surfaces.

"Oral" or "orally" means the oral cavity and/or surfaces of the oral cavity of an animal (e.g., a human), including the teeth and gums, administrated oral delivery oral medicinal delivery.

"Topical" or "topically" means the surface of an animal (e.g., a human), including the skin or other accessible tissues.

As used herein, the term "pharmaceutically active agent" means a composition which, when administered to a human patient, has a biochemical or physiological effect on the patient.

The aspects of the disclosed embodiments relate to stabilized or more stable compositions of volatile compounds as well as methods of making and using them including a mixture of one or more volatile compounds and at least one stabilizer compound, the stabilizer compound includes a compound of formula (I), for example, undecylenic acid methyl ester or any of the other stabilizer compounds included herein where the volatile compounds in the stabilized or more stable volatile compound compositions are less susceptible to volatizing into a gas and remains in a form that can be added to a composition during manufacture as well as administered in a composition in an amount closer to the amount originally included in the composition when formulated with less volatile compounds volatizing away (i.e., lowering the rate of volatilization of the volatile compounds from what it would be for volatile compounds alone) from the original concentration and, thus, lowering the original concentration and diminishing the amount of the volatile compounds originally added.

Volatile compounds include, for example, menthol, eucalyptus, peppermint oil, camphor, wintergreen, jasmine, orange and other citrus oils and the ingredients of both, rosemary, thyme oil, rose oil, sage oil coriander, chamomile, vanilla, etc. and can have various therapeutic and cosmetic benefits as well as some may be pharmaceutically active agents. Citrus oils include, for example, natural and synthetic citrus oils, for example, orange, grapefruit, lemon, mandarin orange, lime, Mexican lime, tangerine, tangelo and blends thereof, as well as citrus aromatics, natural oleo resins, and extracts. Examples of products with synthetic flavors include Carrubba A9047 (an orange flavor) and Noville AN110099 (a citrus mint flavor). Citrus oils typically contain one or more citrus flavor ingredients including, for example, the following: d-limonene, I-limonene, dl-limonene, alpha-citral and beta-citral (geranol), α-terpinene, γ-terpinene, 2-dodecanal, α-pinene, β-pinene, 2-pentenal, cadiene, decylaldehyde, linalool, terpineol, linalyl esters, terpinyl acetate, citronellal, decanal, as well as $C_8$ to $C_{10}$ and $C_{12}$ aldehydes, acids, and esters found in citrus flavors, and mixtures thereof.

The aspects of the disclosed embodiments also relate to stabilized or more stable menthol compositions as well as methods of making and using them including a mixture of menthol and at least one stabilizer compound (also referred to herein as a menthol stabilizer compound or a volatile compound stabilizer compound), the stabilizer compound for menthol includes a compound of formula (I), for example, undecylenic acid methyl ester or any of the other stabilizer compounds included herein where the menthol in the stabilized or more stable menthol compositions is less susceptible to volatizing into a gas and remains in a form that can be added to a composition during manufacture as well as administered in a composition in an amount closer to the amount originally included in the composition when formulated with less menthol volatizing away (i.e., lowering the rate of volatilization of the menthol from what it would be for menthol alone) from the original concentration and, thus, lowering the original concentration and diminishing the amount of the menthol originally added.

Formula (I)

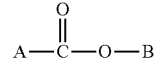

wherein A is —$(CH2)_a$-CH=CH—$(CH 2)_{5-a}$-H where a is from 0 to 5, —$(CH2)_b$-CH=CH—$(CH 2)_{6-b}$-H where b is from 0 to 6, —$(CH2)_c$-CH=CH—$(CH 2)_{7-c}$-H where c is from 0 to 7, —$(CH2)_d$-CH=CH—$(CH 2)_{8-d}$-H where d is from 0 to 8, or —$(CH2)_e$-CH=CH—$(CH2)_{9-d}$-H where d is from 0 to 9; B is hydrogen or $C_{1-5}$ alkyl; and pharmaceutically acceptable salts where B is hydrogen. $C_{1-5}$ alkyl includes straight chain hydrocarbon substituents methyl, ethyl, propyl, butyl and pentyl.

The aspects of the disclosed embodiments also relate to stabilized or more stable volatile compound (e.g., menthol) compositions as well as methods of making and using them including a mixture of menthol and at least one stabilizer compound, the stabilizer compound for volatile compounds (e.g., menthol) includes a compound of formula (I) wherein A is —$(CH2)_d$-CH=CH—$(CH 2)_{8-d}$-H where d is from 0 to 8; B is hydrogen or $C_1$ alkyl; and pharmaceutically acceptable salts where B is hydrogen Embodiments of the present disclosure also relate to stabilized or more stable volatile compound (e.g., menthol) compositions as well as methods of making and using them including a mixture of (a) volatile compound (e.g., menthol) and (b) a stabilizer compound including undecylenic acid (this is the common name used in commerce and among lay individuals; chemical names 10-undecenoic acid) or a salt (preferably a pharmaceutically acceptable salt) thereof or undecylenic acid methyl ester ((this is the common name used in commerce and among lay individuals; chemical names 10-undecenoic acid methyl ester or methyl undec-10-enoate or methyl 10-undecenoate) where the menthol in the stabilized or more stable menthol compositions is less susceptible to volatizing into a gas.

Compounds of Formula (I) also include pharmaceutically acceptable salts where A is —$(CH2)_a$-CH=CH—$(CH 2)_{5-a}$-H where a is from 0 to 5, —$(CH2)_b$-CH=CH—$(CH 2)_{6-b}$-H where b is from 0 to 6, —$(CH2)_c$-CH=CH—$(CH 2)_{7-c}$-H where c is from 0 to 7, —$(CH2)_d$-CH=CH—$(CH 2)_{8-d}$-H where d is from 0 to 8, or —$(CH2)_e$-CH=CH—$(CH 2)_{9-d}$-H where d is from 0 to 9 and B is hydrogen, for example, undecylenic acid salts. Such pharmaceutically acceptable salts may include, for example, inorganic acid addition, hydrochloride salts, sulfate and phosphate salts; and organic acid addition salts, such as alkyl sulfonate, arylsulfonate, acetate, maleate, fumarate, tartrate, citrate and lactate and metal salts including alkali metal salts, such as lithium salt, sodium salt and potassium salt and alkaline earth metal salts, such as magnesium salt and calcium salt, strontium salt, aluminum salt and zinc salt, and other multivalent salts such as for example, zirconium, iron, copper, silver, bismuth etc. Additionally, primary secondary, and tertiary amine salts, organic and inorganic, mono and polyamines compounds could be utilized. Examples include compounds such as urea, and amino acids such as lysine, histidine, arginine etc, could be utilized.

Examples of compounds of Formula (I) include 2-Undecenoic acid; 3-Undecenoic acid; 4-Undecenoic acid; 5-Undecenoic acid; 6-Undecenoic acid; 7-Undecenoic acid; 8-Undecenoic acid; 9-Undecenoic acid; 2-Undecenoic acid methyl ester; 3-Undecenoic acid methyl ester; 4-Undecenoic acid methyl ester; 6-Undecenoic acid ethyl ester; 8-Undecenoic acid methyl ester; 9-Undecenoic acid methyl ester; 10-Undecenoic acid methyl ester; 10-Undecenoic acid ethyl ester; 10-Undecenoic acid propyl ester; 2-Nonenoic acid; 3-Nonenoic acid; 4-Nonenoic acid; 5-Nonenoic acid; 6-Nonenoic acid; 7-Nonenoic acid; 8-Nonenoic acid; 2-decenoic acid; 3-decenoic acid; 4-decenoic acid; 5-decenoic acid; 6-decenoic acid; 9-decenoic acid; ethyl-4-decenoate; ethyl-9-decenoate; butyl-2-decenoate; methyl-2-decenoate; 2-dodecenoic acid; 3-dodecenoic acid; 4-dodecenoic acid; 5-dodecenoic acid; 6-dodecenoic acid; 7-dodecenoic acid; 8-dodecenoic acid; 9-dodecenoic acid; 10-dodecenoic acid; and 11-dodecenoic acid.

The stabilized or more stable volatile compound composition can be incorporated into delivery vehicles and compositions for oral or topical medicinal delivery of the volatile compound by itself or in combination with other active chemical entities, or methods of use or administration thereof.

The stabilized or more stable menthol composition can be incorporated into delivery vehicles and compositions for oral or topical medicinal delivery of the menthol by itself or in combination with other active chemical entities, or methods of use or administration thereof.

Menthol can be used as a flavoring or as a pharmaceutically active agent. It is an organic compound that can be made synthetically or obtained from mint compounds such as corn mint and peppermint. Medicinally, it been found that menthol can have anesthetic (e.g., local) by, for example, blocking nerve signal transmission and counterirritant properties as well as anti-inflammatory properties (e.g., systemic and local) when administered to a patient. In general, the action of local anesthetics can restrict to the site of application and rapidly reverses upon diffusion from the site of action in the nerve. Local anesthetics can also serve an important function in providing peripheral pain relief. Topical administration of pain-relieving anesthetics can provide important advantages over systemic or local, non-topical administration. Furthermore, menthol is a vasodilator that can accelerate the transport of active in the circulatory system. Menthol can also be used as a nasal decongestant to relieve nasal congestion when inhaled. It is also a cooling agent, reduces itching (antipruritic), a topical penetration enhancer, decongestant, pesticide, and perfumery.

Menthol can be in an amount of about 0.1 wt % to about 20 wt %, about 0.1 wt % to about 10 wt %, about 0.1 wt % to about 5.0 wt %, about 0.1 wt % to about 2.5 wt %, about 0.1 wt % to about 1.0 wt %, about 0.1 wt % to about 0.75 wt % or about 0.50 wt % An effective amount of menthol includes an anesthetic, pain reducing (e.g., analgesic) or anti-inflammatory effective amount of menthol.

Embodiments of the present disclosure include stabilized or more stable menthol compositions that can be made by mixing together (a) menthol and (b) a stabilizer compound in a ratio of (a) about 1 molar part menthol to (b) the amount of one or more than one of the stabilizer compounds (the compound of formula (I), undecylenic acid methyl ester, undecylenic acid or a salt (preferably a pharmaceutically acceptable salt) of undecylenic acid, including mixtures thereof) of from about 0.005 molar part to about 1.00 molar part, about 0.010 molar part to about 0.750 molar part, about 0.020 molar part to about 0.50 molar part, about 0.050 molar part to about 0.250 molar part, or about 0.10 molar part. It is believed that the stabilizer compounds (e.g., undecylenic acid methyl ester and others included herein) and menthol may associate to form a menthol analog where the menthol analog's vapor pressure becomes lower than menthol itself. As a result of having a lower vapor pressure, the menthol component of the menthol analog volatizes as a lower rate than menthol by itself. In compositions where there are other components or ingredients in addition to the menthol, the stabilized menthol composition is mixed prior to being added to the other components or ingredients. In other words, the stabilized menthol composition is pre-mixed before being added to the other components or ingredients.

Embodiments of the present disclosure also include stabilized or more stable volatile compound compositions that can be made by mixing together (a) at least one volatile compound and (b) at least one stabilizer compound in a ratio of (a) about 1 molar part volatile compound or compounds to (b) the amount of one or more than one of the stabilizer compounds (e.g., the compound of formula (I), undecylenic acid methyl ester, undecylenic acid or a salt (preferably a pharmaceutically acceptable salt) of undecylenic acid, including mixtures thereof) of from about 0.005 molar part to about 1.00 molar part, about 0.010 molar part to about 0.750 molar part, about 0.020 molar part to about 0.50 molar part, about 0.050 molar part to about 0.250 molar part, or about 0.10 molar part. It is believed that the stabilizer compounds (e.g., undecylenic acid methyl ester and others included herein) and volatile compound or compounds may associate to form a volatile compound analog where the volatile compound analog's vapor pressure becomes lower than menthol itself. As a result of having a lower vapor pressure, the volatile compound component of the volatile compound analog volatizes as a lower rate than menthol by itself. In compositions where there are other components or ingredients in addition to the volatile compound or compounds, the stabilized volatile compound composition is mixed prior to being added to the other components or ingredients. In other words, the stabilized volatile compound composition is pre-mixed before being added to the other components or ingredients.

One possible explanation for the stabilization of the volatile compound or compounds (e.g., menthol) by the compound of formula (I) may be that the menthol and other volatile compounds associate with the alkenyl side chain of the stabilizer compounds may provide a molecular attraction connecting the stabilizer compounds and a volatile compound molecule (e.g., menthol molecule), such that more than one volatile compound molecule (e.g., menthol molecule) may associate with a molecule of one of the stabilizer compounds.

Embodiments of the present disclosure also include stabilized or more stable menthol compositions including menthol and at least one of the menthol stabilizer compounds (e.g., the compound of formula (I), undecylenic acid methyl ester and others included herein) the stabilized or more stable menthol compositions can be made first by dissolving menthol in one or more of a pharmaceutically acceptable suitable solvent capable of dissolving menthol, such as, for example, a low ($C_1$ to $C_5$), medium ($C_6$ to $C_{12}$), or long ($C_{13}$ to $C_{20}$) chain triglyceride. Examples of such solvents are coconut oil, olive oil, palm oil, hemp oil and castor oil. Other acceptable solvents, such as alcohols, ethers and polyalcohols, for example, propylene glycol, butylene glycol, and polyethylene glycols (PEGs) can also be used. The desired amount of at least one of the menthol stabilizer compounds disclosed herein (e.g., the compounds of formula (I), undecylenic acid methyl ester and others disclosed herein) is then added to that mixture. Such compositions that include menthol, solvent and the menthol stabilizer compounds included herein may be made where the mixture of the these ingredients includes a molar ratio of about one molar part menthol to a range of from about 0.0050 molar part to about 1.00 molar part, about 0.010 molar part to about 0.750 molar part, about 0.020 molar part to about 0.50 molar part, about 0.050 molar part to about 0.250 molar part, or about 0.10 molar part of at least one of the menthol stabilizer compounds (i.e., one of the menthol stabilizer compounds or a mixture of more than one of the menthol stabilizer compounds) included herein, preferably a molar ratio of about one molar part menthol to at most about 0.50 molar part, at most about 0.250 molar part or at most about 0.10 molar part of one or more than one of the menthol stabilizer compounds included herein. Such mixtures of menthol, solvent and menthol stabilizer compounds may be used when smaller amounts of menthol need to be stabilized (where the amount of menthol stabilizer compound to be mixed with the menthol is so small that there is not enough of it to dissolve the menthol).

Both stabilized or more stable menthol compositions (i.e., where the menthol is first dissolved in a solvent then dissolved in a menthol stabilizer compound included herein or where the menthol is directly dissolved in a menthol stabilizer compound included herein) can be used in orally administered and non-orally administered compositions (e.g., non-orally topically administered compositions (e.g., place on the skin or other external tissues)). However, the menthol stabilizer compounds can have a bitter taste. The dissolving of the menthol in solvent prior to the addition of at least one of the menthol stabilizer compounds included herein is preferably used in menthol containing therapeutic compositions to be administered orally because by first dissolving the menthol in a suitable solvent, less of the menthol stabilizer compounds may be used, thus lessening the bitter taste of the menthol stabilized composition and the final product in which it is included that is imparted by the menthol stabilizer compound.

Embodiments of the present disclosure also include stabilized or more stable volatile compound compositions including at least one volatile compound and at least one of the stabilizer compounds (e.g., the compound of formula (I), undecylenic acid methyl ester and others included herein) the stabilized or more stable volatile compound compositions can be made first by dissolving the volatile compound or compounds in one or more of a pharmaceutically acceptable suitable solvent capable of dissolving the volatile compound, such as, for example, a low, medium, or long chain triglyceride. Examples of such solvents are coconut oil, olive oil, palm oil, hemp oil and castor oil. Other acceptable solvents, such as alcohols, ethers and polyalcohols, for example, propylene glycol, butylene glycol, and polyethylene glycols (PEGs) can also be used. The desired amount of at least one of the stabilizer compound disclosed herein (e.g., the compounds of formula (I), undecylenic acid methyl ester and others disclosed herein) is then added to that mixture. Such compositions that include volatile compound or compounds, solvent and the stabilizer compounds included herein may be made where the mixture of the these ingredients includes a molar ratio of about one molar part volatile compound or compounds to a range of from about 0.0050 molar part to about 1.00 molar part, about 0.010 molar part to about 0.750 molar part, about 0.020 molar part to about 0.50 molar part, about 0.050 molar part to about 0.250 molar part, or about 0.10 molar part of at least one of the stabilizer compounds (i.e., one of the stabilizer compounds or a mixture of more than one of the stabilizer compounds) included herein, preferably a molar ratio of about one molar part volatile compound or compounds to at most about 0.50 molar part, at most about 0.250 molar part or at most about 0.10 molar part of one or more than one of the stabilizer compounds included herein. Such mixtures of volatile compound or compounds, solvent and stabilizer compounds may be used when smaller amounts of volatile compound or compounds need to be stabilized (where the amount of stabilizer compound to be mixed with the volatile compound or compounds is so small that there is not enough of it to dissolve the volatile compound or compounds).

Both stabilized or more stable volatile compound compositions (i.e., where the volatile compound is first dissolved in a solvent then dissolved in a stabilizer compound included herein or where the volatile compound is directly dissolved in a stabilizer compound included herein) can be used in orally administered and non-orally administered compositions (e.g., non-orally topically administered compositions (e.g., place on the skin or other external tissues)). However, the stabilizer compounds can have a bitter taste. The dissolving of the volatile compound in solvent prior to the addition of at least one of the stabilizer compounds included herein is preferably used in volatile compound containing therapeutic compositions to be administered orally because by first dissolving the volatile compound in a suitable solvent, less of the stabilizer compound may be used, thus lessening the bitter taste of the volatile compound stabilized composition and the final product in which it is included that is imparted by the stabilizer compound.

Compositions of the present disclosure can include other pharmaceutically active agents including, but not limited to analgesics, decongestants, bronchodilators and other antiasthmatic agents, cardiovascular agents such as beta-blockers, ACE inhibitors, diuretics, antithrombics, etc., diabetic agents, antihistamines, anesthetics, antifungals, antinauseants, antiemetics, antibacterial agents, antifungal agents, corticosteroids, neurological agents, anti-inflammatories, vaccines, biological agents (such as Humera, Enbrel and Remicade), wound healing agents and anticonvulsants. Vitamins (particularly A, C, D and E) are also exemplary pharmaceutically active agents Cannabinoids are a pharmaceutically active agent and a class of chemical compounds that can be derived from plants (phytocannabinoids that include Cannabidiol (CBD) including, for example, CBD oil, Cannabinol (CBN) and tetrahydrocannabinol (THC), the latter being a known psychotropic compound and the first two being non-psychotropic) or synthetically produced, such as, for example, phytocannabinoids including Cannabidiol (CBD) and full spectrum hemp oil that is oil derived from the entire plant except the flower (which contains THC) and can have over 85 phytocannabinoids.

Embodiments of the present disclosure also include various compositions and formulations into which the stabilized or more stable menthol compositions can incorporated optionally along with other additional ingredients. Such compositions and formulations can be, for example, various therapeutic, cosmetic and confectionary products, compositions and formulations. Therapeutic products, compositions and formulations can include the volatile compound or compounds (e.g., menthol) as well as optionally other ingredients (including other medicinal and/or therapeutic compounds, other pharmaceutically active agents) for the purpose of treating or preventing a disease, physical malady or symptoms thereof and the remedial actions thereof. Cosmetic products, compositions and formulations can include the volatile compound or compounds (e.g., menthol) as well as optionally other ingredients (including other medicinal and/or therapeutic compounds, other pharmaceutically active agents) for its use involving or relating to treatment intended to restore or improve a person's appearance including skincare and other external parts of the body (e.g., face, lips, scalp, nails, etc.). Confectionery products, compositions and formulations can include the volatile compound or compounds (e.g., menthol) as well as optionally other ingredients (including other medicinal and/or therapeutic compounds, other pharmaceutically active agents) and can include candies, candied nuts, chocolates, chewing gum, bubble gum, pastillage, and other confections that are made primarily of sugar and/or chocolate or other confectionary ingredients.

Delivery vehicles for such products that are pharmaceutically acceptable, topically acceptable and/or orally acceptable can include a pharmaceutically acceptable carrier, diluent or excipient" and be in the form of, for example, tablets or capsules (including gelatin capsules); liquid preparations, for example, solutions, syrups or suspensions; rectal compositions such as suppositories or retention enemas, lotions, creams, ointments, powders, gels; transdermal delivery systems, patches, vehicles and devices including those for oral transdermal delivery by being placed on tissues in the oral cavity or on exposed body parts of an animal (e.g., human, dog, cat, etc.); chewing gum and lozenge compositions, products and devices (e.g., chewing gum and lozenges including those that are unfilled and filled including liquid-filled or solid or semi-solid filled); and dissolvable thin oral tapes, films or strips or segments thereof; delivery matrixes including polymer matrixes such as, for example, an absorbent polymer (e.g., a superabsorbent polymer), hydrogels (formed by combining a biocompatible polymer with a polyalcohol); and modified release formulations. "Pharmaceutically acceptable carrier, diluent or excipient" includes without limitation any carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Example 1

Mixing menthol (about 10 g.) and undecylenic acid methyl ester (about 10 g.) until the menthol is uncrystallized and dissolved in the undecylenic acid methyl ester.

Example 2

Mixing menthol (about 1.0 g.) and coconut oil (about 3.0 g.) at 76 degree F. until the menthol is uncrystallized and dissolved in the coconut oil. Then the undecylenic acid methyl ester (about 0.005 g.) is added to the menthol/coconut oil mixture.

Example 3

Mixing menthol (about 0.1 g.) and hemp oil at room temperature (about 3.0 g.) at room temperature until the menthol is uncrystallized and dissolved in the hemp oil. Then the undecylenic acid methyl ester (about 0.005 g.) is added to the menthol/hemp oil mixture.

All publications, including but not limited to, issued patents, patent applications, and journal articles, cited in this application are each herein incorporated by reference in their entirety.

Thus, while there have been shown, described and pointed out, fundamental novel features of the present disclosure as applied to the exemplary embodiments thereof, it will be understood that various omissions and substitutions and changes in the form and details of devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While there have been shown, described and pointed out, fundamental features of the present disclosure as applied to the exemplary embodiments thereof, it will be understood that various omissions and substitutions and changes in the form and details of compositions, devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

The invention claimed is:

1. A stabilized menthol composition or composition for lowering the rate of volatilization of menthol consisting essentially of: menthol; and a menthol stabilizer compound including methyl 10-undecenoate; and optionally a solvent.

2. The composition of claim 1, wherein the stabilized menthol composition or composition for lowering the rate of volatilization of menthol includes a ratio of about 1 molar part menthol to from about 0.005 molar part to about 1.0 molar part of the menthol stabilizer compound.

3. The composition of claim 1, wherein the stabilized menthol composition or composition for lowering the rate of volatilization of menthol includes a ratio of about 1 molar part menthol to from about 0.010 molar part to about 0.50 molar part of the menthol at stabilizer compound.

4. The composition of claim 1, wherein the stabilized menthol composition or composition for lowering the rate of volatilization of menthol includes a ratio of about 1 molar part menthol to from about 0.050 molar part to about 0.250 molar part of the menthol stabilizer compound.

5. The composition of claim 1, wherein the stabilized menthol composition or composition for lowering the rate of volatilization of menthol includes a ratio of about 1 molar part menthol to from about 0.020 molar part to about 0.750 molar part of the menthol stabilizer compound.

6. The composition of claim 1, wherein the stabilized menthol composition or composition for lowering the rate of volatilization of menthol includes a ratio of about 1 molar part menthol to about 0.10 molar part of the menthol stabilizer compound.

7. The composition of claim 1, wherein the solvent is one or more of a low, medium or long chain triglycerides including coconut oil, olive oil, palm oil, hemp oil or castor oil; one or more alcohols; one or more ethers; or one or more polyalcohols including propylene glycol, butylene glycol, or polyethylene glycols (PEGs).

8. A stabilized menthol composition or composition for lowering the rate of volatilization of menthol consisting essentially of: menthol; and at least one menthol stabilizer compound, the at least one menthol stabilizer compound including 10-undecenoic acid or a salt of 10-undecenoic acid; and a solvent capable of dissolving the menthol, wherein the stabilized menthol composition or composition for lowering the rate of volatilization of menthol includes a ratio of about 1 molar part menthol to from about 0.005 molar part to about 1.0 molar part of the at least one of the stabilizer compounds.

9. The composition of claim 8, wherein the stabilized menthol composition or composition for lowering the rate of volatilization of menthol includes a ratio of about 1 molar part menthol to from about 0.010 molar part to about 0.50 molar part of the at least one of the stabilizer compounds.

10. The composition of claim 8, wherein the stabilized menthol composition or composition for lowering the rate of volatilization of menthol includes a ratio of about 1 molar part menthol to from about 0.050 molar part to about 0.250 molar part of the at least one of the stabilizer compounds.

11. The composition of claim 8, wherein the stabilized menthol composition or composition for lowering the rate of volatilization of menthol includes a ratio of about 1 molar part menthol to from about 0.020 molar part to about 0.750 molar part of the at least one of the stabilizer compounds.

12. The composition of claim 8, wherein the stabilized menthol composition or composition for lowering the rate of volatilization of menthol includes a ratio of about 1 molar part menthol to about 0.10 molar part of the at least one of the stabilizer compounds.

13. The composition of claim 8 wherein the solvent is one or more of a low, medium or long chain triglycerides including coconut oil, olive oil, palm oil, hemp oil or castor oil; one or more alcohols; one or more ethers; or one or more polyalcohols including propylene glycol, butylene glycol, or polyethylene glycols (PEGs).

14. A composition comprising:
a stabilized menthol composition or composition for lowering the rate of volatilization of menthol consisting essentially of: menthol; at least one menthol stabilizer compound, the at least one menthol stabilizer compound including 10-undecenoic acid or a salt of 10-undecenoic acid; and a solvent capable of dissolving the menthol, wherein the stabilized menthol composition or composition for lowering the rate of volatilization of menthol includes a ratio of about 1 molar part menthol to from about 0.005 molar part to about 1.0 molar part of the at least one of the stabilizer compounds; and
at least one of a pharmaceutically active agent and a delivery vehicle,
wherein the stabilized menthol composition or composition for lowering the rate of volatilization of menthol is formed prior to being added to the at least one of the pharmaceutically active agent and the delivery vehicle.

15. The composition of claim 14, wherein the stabilized menthol composition or composition for lowering the rate of volatilization of menthol includes a ratio of about 1 molar part menthol to from about 0.005 molar part to about 1.0 molar part of the at least one of the stabilizer compounds.

16. The composition of claim 14, wherein the stabilized menthol composition or composition for lowering the rate of volatilization of menthol includes a ratio of about 1 molar part menthol to from about 0.050 molar part to about 0.250 molar part of the at least one of the stabilizer compounds.

17. The composition of claim 14, wherein the stabilized menthol composition or composition for lowering the rate of volatilization of menthol includes a ratio of about 1 molar part menthol to from about 0.020 molar part to about 0.750 molar part of the at least one of the stabilizer compounds.

18. The composition of claim 14, wherein the stabilized menthol composition or composition for lowering the rate of volatilization of menthol includes a ratio of about 1 molar part menthol to about 0.10 molar part of the at least one of the stabilizer compounds.

19. The composition of claim 14, wherein the solvent is one or more of a low, medium or long chain triglycerides including coconut oil, olive oil, palm oil, hemp oil or castor oil; one or more alcohols; one or more ethers; or one or more polyalcohols including propylene glycol, butylene glycol, or polyethylene glycols (PEGs).

20. A composition comprising:
a stabilized menthol composition or composition for lowering the rate of volatilization of menthol consisting essentially of: menthol; a menthol stabilizer compound including methyl 10-undecenoate; and optionally a solvent capable of dissolving the menthol; and
at least one of a pharmaceutically active agent and a delivery vehicle,
wherein the stabilized menthol composition or composition for lowering the rate of volatilization of menthol is formed prior to being added to the at least one of the pharmaceutically active agent and the delivery vehicle.

* * * * *